US00PP25201P2

(12) United States Plant Patent
Brouwer

(10) Patent No.: US PP25,201 P2
(45) Date of Patent: Dec. 30, 2014

(54) ***SPATHIPHYLLUM* PLANT NAMED '500JET'**

(50) Latin Name: ***Spathiphyllum* hybrid**
Varietal Denomination: 500JET

(71) Applicant: Wim Brouwer, Nootdorp (NL)

(72) Inventor: Wim Brouwer, Nootdorp (NL)

(73) Assignee: ISB Holland (NL)

( * ) Notice: Subject to any disclaimer, the term of this patent is extended or adjusted under 35 U.S.C. 154(b) by 91 days.

(21) Appl. No.: 13/815,381

(22) Filed: Feb. 26, 2013

(51) Int. Cl.
*A01H 5/00* (2006.01)

(52) U.S. Cl.
USPC ..... Plt./364

(58) Field of Classification Search
USPC ..... Plt./364
See application file for complete search history.

*Primary Examiner* — Annette Para

(57) ABSTRACT

A new and distinct *Spathiphyllum* cultivar named '500JET' is disclosed, characterized by large, dark green, foliage, strong, fast growing plants and clear white spathes. The new variety is commercially suitable for indoor plant production.

1 Drawing Sheet

Latin name of the genus and species: *Spathiphyllum* hybrid.

Variety denomination: '500JET'.

BACKGROUND OF THE INVENTION

The new cultivar is a product of a planned breeding program. The new variety originated from a cross pollination, made by the inventor, of a proprietary unpatented seed parent and a proprietary, unpatented pollen parent, both *Spathiphyllum* hybrids. The crossing was performed at a commercial greenhouse in the Netherlands during April of 2007.

The new variety was discovered by the inventor, Wim Brouwer, a citizen of the Netherlands, in Feb. 10, 2008 in a group of seedlings resulting from the crossing. The new cultivar was found in a commercial greenhouse belonging to the inventor in Nootdorp, the Netherlands.

Asexual reproduction of the new cultivar '500JET' was first performed in the Netherlands by tissue culture Mar. 14, 2010. '500JET' has been reproduced by micro-propagation and has shown that the unique features of this cultivar are stable and reproduced true to type.

SUMMARY OF THE INVENTION

The cultivar '500JET' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of '500JET.' These characteristics in combination distinguish '500JET' as a new and distinct *Spathiphyllum* cultivar:

1. Dark green foliage.
2. Large foliage.
3. Clear white spathes.
4. Durable and easy to grow plant
5. Fast growth habit.

PARENTAL COMPARISON

Plants of the new cultivar '500JET' cannot be compared to the seed parent as records of those characteristics were not kept. '500JET' is similar to the pollen parent in most characteristics, however, '500JET' has larger, darker colored foliage.

COMMERCIAL COMPARISON

'500JET' can be compared to compared to the commercial variety *Spathiphyllum* 'Jetty' U.S. Plant Pat. No. 9,957. Plants of 'Jetty' are similar to plants of '500JET' in most horticultural characteristics, however, '500JET' grows faster than 'Jetty' and produces flowers that are more clear white.

BRIEF DESCRIPTION OF THE PHOTOGRAPH

The accompanying photograph in FIG. 1 illustrates in full color a typical plant of '500JET' grown in a greenhouse in Apopka, Fla. This plant is approximately 9 months old, shown in a 6 inch pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe '500JET' plants grown in a climate controlled greenhouse in Apopka, Fla., USA. Temperatures ranged from 18° C. to 22° C. at night to 18° C. to 22° C. during the day. No artificial light, photoperiodic treatments or chemical treatments were given to the plants. Measurements and numerical values represent averages of typical plant types.

Botanical classification: *Spathiphyllum* hybrid '500JET.'

PROPAGATION

Time to initiate roots: Approximately 18 days at approximately 25° C. soil temperature.
Time to produce a fully rooted plantlet: Approximately 14 weeks at approximately 20 to 30° C. soil temperature.
Root description: Thick, fleshy roots with fine, fibrous lateral roots. Color near Orange-White 158C.

PLANT

Growth habit: Leaves growing directly from base of plant, with no stems.
Plant shape: Upright, leaves slightly arching downward.
Height: Approximately 50 cm.
Plant spread: Approximately 45 cm in a 6 inch pot.
Growth rate: Moderate.
Branching characteristics: No branching. Leaves emerge direct from base of plant.
Number of clumps of leaves: 10.
Number of leaves per clump: Average 7.
Number of leaves per plant: Approximately 70.
Age of plant described: Approximately 9 months.
Pot size of plant described: 6 inch.

FOLIAGE

Leaf:
*Arrangement*.—Single leaves emerging basally.
*Average length(excluding petiole)*.—Average 38.5 cm.
*Average width*.—Average 14.8 cm.
*Shape of blade*.—Elliptic.
*Aspect*.—Slightly recurved.
*Apex*.—Apiculate.
*Base*.—Attenuate.
*Margin*.—Entire.
*Texture of top surface*.—Smooth, moderately glossy.
*Texture of bottom surface*.—Smooth, moderately glossy.
*Color*.—Young foliage upper side: Near R.H.S. Green139B. Young foliage under side: Near R.H.S. Green 137A. Mature foliage upper side: Near R.H.S. Green139A. Mature foliage under side: Near R.H.S. Green141C.
Venation:
*Type*.—Pinnate.
*Venation coloration upper side*.—Green 143A.
*Venation coloration under side*.—Green 143C.
Petiole(excluding Geniculum):
*Length*.—Approximately 28 cm.
*Width*.—At geniculum: Approximately 0.6 cm. Above clump: Approximately 1.1 cm.
*Color*.—Near RHS Green 139B.
*Strength*.—Moderate.
Geniculum:
*Length*.—Approximately 3.2 cm.
*Width*.—Approximately 0.6 cm.
*Color*.—Near RHS Green 143A.

INFLORESCENCE

*Arrangement*.—Spathes with spadices held above the foliage on erect peduncles arising from the petiole sheath.
*Flowering habit*.—Continuous.
*Quantity of spathes per plant*.—On average 3 to 6 fully open spathes in good condition.
*Natural flowering season*.—Autumn to Winter.
*Time to flowering*.—6 months.
*Fragrance*.—Very slight. Sweet.
*Self-cleaning or persistent*.—Persistent.
*Flower longevity*.—Flowers stay in good condition approximately 6 to 12 weeks on the plant.
Spathe:
*Aspect*.—Slightly concave. More concave at base, mostly flat moving towards apex.
*Length*.—Average 14 cm.
*Width*.—Average 7.2 cm.
*Shape*.—Elliptic.
*Margin*.—Entire.
*Apex*.—Apiculate.
*Base*.—Cuneate.
*Color*.—Front when opening: Near RHS White 155C. Back when opening: Near RHS White 155C. Front when mature: Near RHS White N155A. Back when mature: Near RHS White 155C. Fading to: No fading.
Spadix:
*Shape*.—Columnar, arising from the top of the peduncle.
*Tip*.—Obtuse.
*Base*.—Obtuse.
*Length*.—Approximately 6.5 cm.
*Width*.—Approximately 1.4 cm.
*Color*.—When opening: Near RHS Yellow-White 158C. Mature: Near RHS Yellow-White 158A.
*Quantity of flowers per spadix*.—Approximately 100.
*Spadix flower arrangement*.—Bisexual, rounded.
*Spadix flower diameter*.—Approximately 0.2 cm.
*Spadix flower depth*.—Approximately 0.1 cm.
Peduncle:
*Length*.—Approximately 35 cm.
*Width*.—Approximately 0.8 cm.
*Color*.—Near RHS Green 139B.
*Strength*.—Moderate.

REPRODUCTIVE ORGANS

*Ovary color*.—Near RHS 155B.
*Stigma color*.—Near RHS 155B.
*Anther color*.—Near RHS 155A.
*Quantity of pollen*.—Scant.
*Pollen color*.—Near RHS 155A.

OTHER CHARACTERISTICS

Disease resistance: Neither resistance nor susceptibility to diseases or pests has been observed in this variety.
Drought tolerance and cold tolerance: The new cultivar is a typical *Spathiphyllum*, cold tolerant to approximately 5 to 7° C. and does not tolerate drought.
Fruit/seed production: Not observed.

What is claimed is:

1. A new and distinct cultivar of *Spathiphyllum* plant named '500JET' as herein illustrated and described.

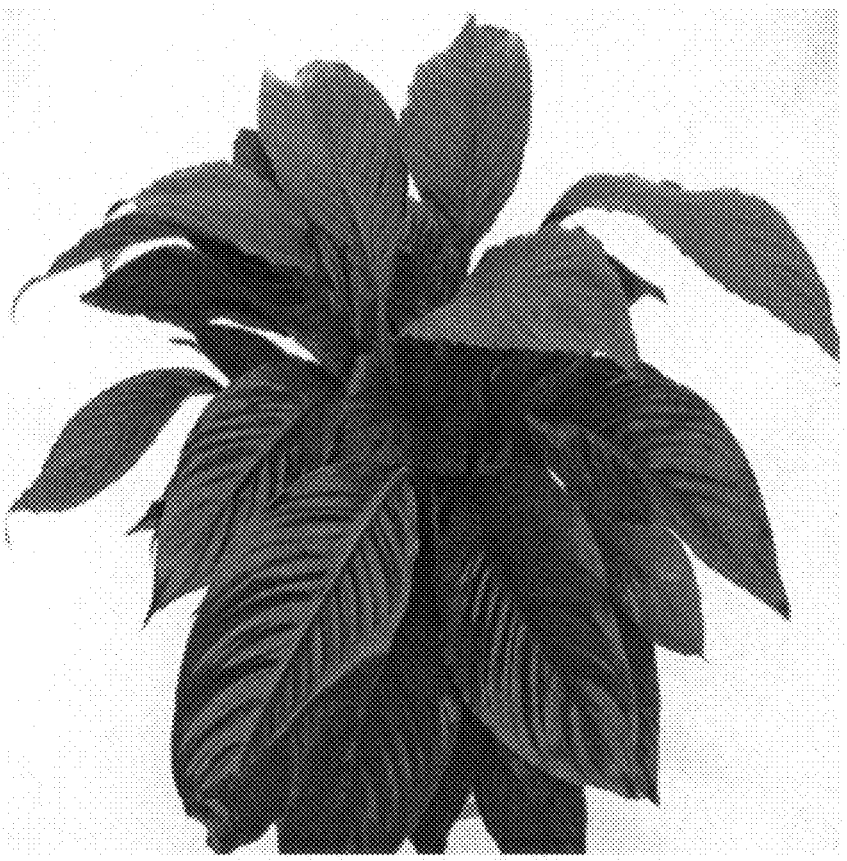

* * * * *